United States Patent [19]

Rock

[11] 4,383,989
[45] May 17, 1983

[54] FACTOR VIII CONCENTRATES PREPARED FROM HEPARINIZED PLASMA BY THE APPLICATION OF A COLD PRECIPITATION TECHNIQUE

[76] Inventor: Gail A. Rock, 270 Sandridge Rd., Rockcliffe Park, Ontario, Canada, K1L 5A2

[21] Appl. No.: 317,312

[22] Filed: Nov. 2, 1981

[30] Foreign Application Priority Data

Oct. 1, 1981 [CA] Canada ................... 387063

[51] Int. Cl.$^3$ ........................... A61K 35/14
[52] U.S. Cl. ...................... 124/101; 424/94; 424/177
[58] Field of Search .............. 424/101, 177, 94

[56] References Cited

U.S. PATENT DOCUMENTS

| Re. 29,698 | 7/1978 | Fekete et al. | 260/112 B |
|---|---|---|---|
| 3,803,115 | 4/1974 | Fekete et al. | 260/112 B |
| 4,203,891 | 5/1980 | Rock | 260/112 B |
| 4,210,580 | 7/1980 | Amrani | 424/101 |
| 4,289,691 | 9/1981 | Rock et al. | 424/101 |

Primary Examiner—Sam Rosen
Attorney, Agent, or Firm—Holman & Stern

[57] ABSTRACT

A method for recovering Antihemophilic Factor VIII from whole blood or blood plasma or blood plasma fractions freshly collected directly into an anticoagulant selected from the group of heparin, sodium heparin, or mixtures thereof, the heparin being used in the range of 6-8 units/ml of plasma or 3.5-4 units/ml of blood; and either first separating the red cells from the plasma and/or freezing the heparinized plasma, resolubilizing the plasma, isolating a cryoprecipitate from the plasma, resolubilizing the cryoprecipitate, adding a saline heparin solution to the resolubilized cryoprecipitate, incubating the resolubilized cryoprecipitate at a temperature of from about 0° C. to about 4° C. for a time of at least 2 hours, whereby Factor VIII present in the cryoprecipitate is insolubilized using heparin precipitable cold insoluble globulin and the resulting Factor VIII rich precipitate also includes cold insoluble globulin, separating the Factor VIII rich precipitate, and isolating Factor VIII therefrom. This new process permits recovery of a high purity Factor VIII preparation which can easily be made in the blood bank or alternatively, the cold precipitation step can be carried out in a fractionation plant.

3 Claims, 1 Drawing Figure

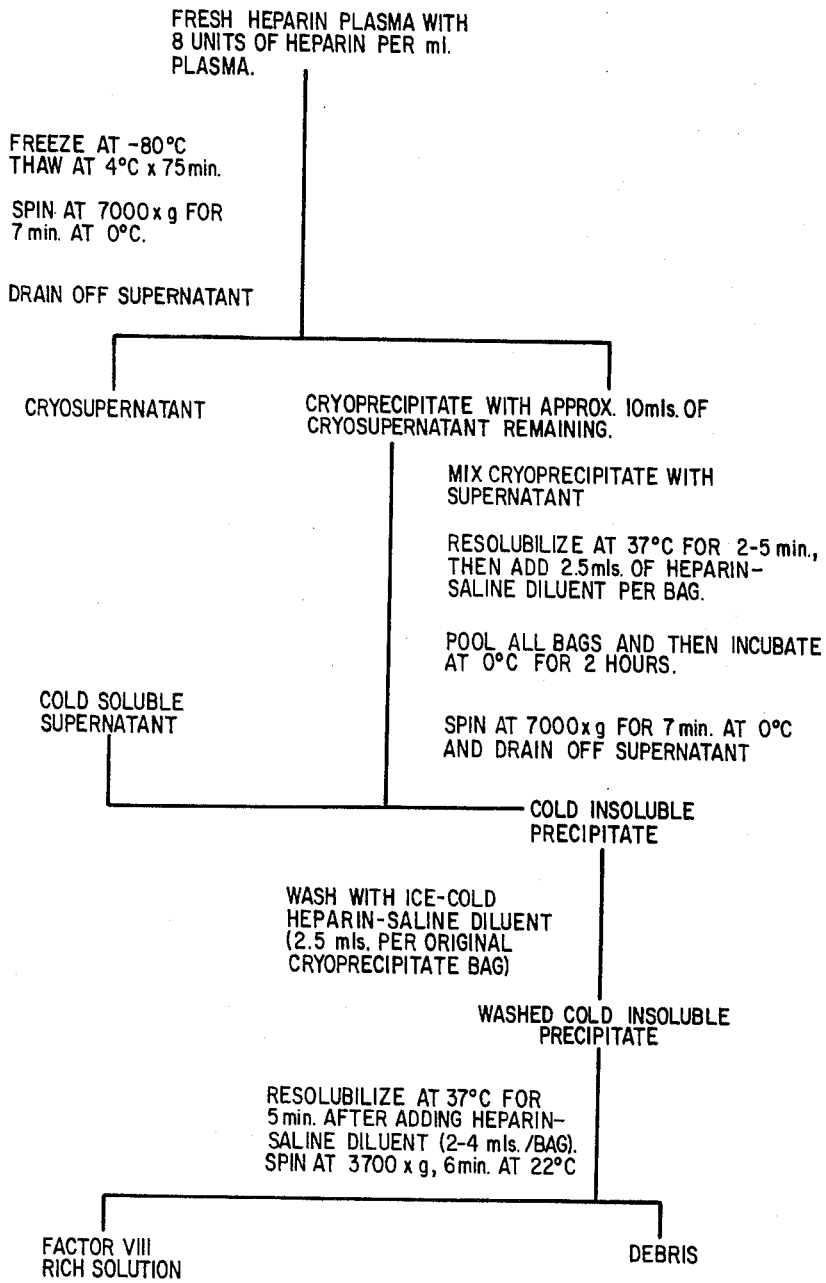

FACTOR VIII CONCENTRATES PREPARED FROM HEPARINIZED PLASMA BY THE APPLICATION OF A COLD PRECIPITATION TECHNIQUE

This invention is concerned with the preparation of Factor VIII concentrates by a method involving an improved method for the application of a cold precipitation technique to purify the Factor VIII protein.

In U.S. Pat. No. 4,203,891 issued May 20, 1980 to Gail A. Rock there is described a method of greatly increasing the yield of Antihemophilic Factor VIII (AHF) obtained from whole blood, blood plasma or blood plasma fractions based on the maintenance of physiological concentrations of calcium and/or other ions in the whole blood or plasma components. In the method described an attempt was made to preserve the initial Factor VIII activity in plasma as much as possible while at the same time to improve the recovery of Factor VIII in cryoprecipitate prepared from that plasma.

In U.S. Pat. No. 4,289,691, issued Sept. 15, 1981 in the name of Gail Ann Rock and Douglas Stephen Palmer (corresponds to Canadian application Ser. No. 344,000 filed Jan. 18, 1980), there is described a method of obtaining Factor VIII which involves the introduction of a cold insoluble globulin (CIg) or fibronectin step to Factor VIII production which results in markedly increased yields of Factor VIII in the cryoprecipitate and, as well, in the cold-insoluble globulin or fibronectin obtained from the cryoprecipitate. As was discussed in the disclosure of the aforementioned patent application, the cold precipitation of fibronectin and fibrinogen had been an established procedure for many years prior to the filing date of the original Fekete patent in 1972 now Re. 29,698, issued July 11, 1978. It was generally known that addition of heparin or some other polysaccharide compound was necessary in order to effect precipitation of fibronectin in the cold. However, at no point had the literature suggested or contained directions for the application of a cold-insoluble globulin or fibronectin purification step toward the production of Factor VIII. In fact, a 1975 paper by Mosher, entitled "Cross Linking of Cold-Insoluble Globulin by Fibrin-Stabilizing Factor", published in J.B.C. 250: 6614, 1975, indicated that cold-insoluble globulin was distinguished from antihemophilic factor (Factor VIII) by amino acid analysis, by the position of elution from 4% agarose gels and by the electrophoretic migration in polyacrylamide gels.

Thus the invention of that previous U.S. Pat. No. 4,289,691 dealt with the application of a procedure for production of fibronectin or cold-insoluble globulin (CIg) to the production of Factor VIII. The introduction of the cold-insoluble globulin cryoprecipitation step to Factor VIII production resulted in markedly increased yields of Factor VIII in the cryoprecipitate and, as well, in the subsequent cold-insoluble globulin fraction obtained from the cryoprecipitate. Using this procedure, 81% of the Factor VIII was recovered in the cryoprecipitate. The subsequent cold-insoluble globulin fraction contained 62% of the starting Factor VIII activity. A final recovery of 666 units per liter of starting plasma was therefore obtained and the amount of protein was reduced to less than 1% compared to starting plasma. In addition the procedure could be carried out in blood donor centers, although it was also envisaged to be useful in larger scale recovery of Factor VIII procedures. In the method described, the efficiency of the cryoprecipitate obtained from CPD (citrate phosphate dextrose anticoagulant) plasma was improved by the addition of heparin anticoagulant and the use of a cold incubation step with citrate saline heparin buffer. It is to be noted that the best results described in this application were obtained when 1 unit heparin/ml of plasma was used. This amount of heparin was found to produce an optimum result wherein the cryoprecipitate efficiency increased so that a yield up to 80% of Factor VIII was obtained. In addition some improvement of initial or zero activity was also obtained. As a comparison, the cryoprecipitate efficiency of plasma collected into conventional anticoagulants generally ranges from 40–50%. Thus, the cold-insoluble globulin technique offered a far superior method for isolating intermediate purity Factor VIII.

It has now been found that the cold-insoluble globulin technique can be applied to cryoprecipitates obtained from blood or plasma collected into heparin or sodium heparin or mixtures of the two to obtain a high purity Factor VIII. More specifically, the process of collecting blood or blood plasma into heparin together with the cold incubation step produces a cold insoluble globulin-like material which is very rich in Factor VIII. This new process permits recovery of a high purity Factor VIII preparation which can easily be made in the blood bank or alternatively, the cold precipitation step can be carried out in a fractionation plant.

Thus this invention provides a method of obtaining Factor VIII which comprises
(a) adding heparin to freshly obtained blood plasma collected into a calcium chelating anticoagulant or collecting blood plasma by plasma pheresis using heparin and a calcium chelating anticoagulant;
(b) freezing the plasma;
(c) resolubilizing the plasma;
(d) isolating a cryoprecipitate from the plasma;
(e) resolubilizing the cryoprecipitate;
(f) adding a citrate saline heparin buffer to the resolubilized cryoprecipitate;
(g) incubating the buffered, resolubilized cryoprecipitate at a temperature of from about 0° to 10° C. for a time in excess of about one hour, whereby Factor VIII present in the cryoprecipitate is insolubilized using heparin precipitable cold insoluble globulin and the resulting (Factor VIII) rich precipitate also includes cold insoluble globulin;
(h) separating the Factor VIII rich precipitate; and
(i) isolating Factor VIII therefrom,
the improvement consisting of:
(1) substituting for step (a) collecting freshly obtained blood plasma or blood plasma fractions directly into an anticoagulant consisting essentially of heparin, sodium heparin, or their mixture, in a proportion of about 6–8 units of heparin per ml of blood plasma, in the absence of a calcium chelating anticoagulant; and
(2) substituting for step (f), adding a buffer consisting essentially of a saline heparin solution to the resolubilized cryoprecipitate, in the absence of a citrate buffer.

As indicated above, the blood is freshly collected directly into heparin, using approximately 6–8 units/ml, preferably 8 units/ml of plasma or is prepared by plasmapheresis using heparin as anticoagulant rather than citrate phosphate dextrose (CPD). Where required, the red cells are separated from the plasma and then the plasma is frozen according to standard blood bank technique and cryoprecipitate is made from plasma. The cryoprecipitates are then solubilized and pooled according to the method for obtaining a cold insoluble precipitate as previously described.

Although a saline heparin solution is used with this technique, and it is preferred, it is also possible to employ a citrate saline heparin buffer as described in the aforementioned U.S. Pat. No. 4,289,591. However, use of the citrate saline heparin buffer does lower the yields of Factor VIII and obviously therefore this buffer is less practical than the saline heparin buffer.

The method of this invention may be described in precise terms as follows. Fresh heparin plasma at 8 units heparin per ml is frozen to −80° C., then resolubilized at 4° C. for 75 minutes, after which it is centrifuged (spin 7000×g, 7 min at 0° C.). The resulting cryoprecipitate is allowed to resolubilize at 37° C. for 2–5 minutes, after which 2.5 ml heparin saline buffer, pH 7.2 per cryoprecipitate bag is added. The resolubilized, pooled cryoprecipitate is then incubated at 0° C. for two hours in a refrigerated water bath. The Factor VIII present in the cryoprecipitate pool now insolubilizes along with the cold-insoluble globulin, and the total insoluble precipitate is then separated from the Factor VIII poor supernatant by centrifugation (spin 7000×g, 7 min at 0° C.). After draining off the supernatant, the cold-insoluble precipitate is washed at 0° C. with 2–4 ml of cold saline heparin solution per original bag, drained and allowed to resolubilize at 37° C. for five minutes with from 2–10 ml, preferably 2 ml saline heparin solution per original cryoprecipitate bag. A further centrifugation at 22° C. (spin 3700×g, 6 min) is conducted and the Factor VIII rich solution in the supernatant is separated from the sedimented debris.

In the drawing which is used to illustrate this invention there is shown a flow sheet which helps to illustrate the specific steps of this procedure as have just been described.

Using this new technique as can be seen from the tables below, it is possible to obtain a high purity, high yield Factor VIII product with recovery of more than 50% of the starting Factor VIII activity and a final yield in the range of 800 units per liter of starting plasma.

In the aforementioned patent application, the final product is often an intermediate purity Factor VIII, whereas the present technique always produces a high purity product. This is most advantageous, since it eliminates the need for the addition of chemical precipitants, such as those employed in Cohn fractionation techniques, ie. ethanol and salts or others such as ammonium sulphate, polyethylene glycol, or polyelectrolytes. In addition, no pH adjustments are required.

The resulting material can by lyophilized or otherwise prepared for storage and infusion.

TABLE 1

Heparin Plasma Fractionation by the Cold-Insoluble Cryoprecipitate Technique

| Fraction | Total Units of F.VIII:C | Total Protein | Specific Activity | Purity Over Plasma | Recovery Per Liter Plasma |
|---|---|---|---|---|---|
| Plasma Pool | 2246 U (100%) | 135,479 mg (100%) | 0.0166 U per mg | 1x | 1500 Units per liter |
| Cryoprecipitate Pool+ | 1814 U (81%) | 5,409 mg (4%) | 0.3354 U per mg | 20.2x | 1211 Units per liter |
| Cold-Insoluble Cryoprecipitate | 1193 U (53%) | 1,208 mg (0.9%) | 0.99 U per mg | 60x | 797 Units per liter |

+resolubilized as required in heparin - saline diluent (heparin at 1 unit per ml, 0.9% NaCl, pH 7.2).

TABLE 2

| Fraction | Analysis of Contents | | | | |
|---|---|---|---|---|---|
| | Total Protein | Total Fibrinogen | Total Albumin | Antibody Titre | Volume |
| Plasma Pool | 135,479 mg (100%) | 2964 mg (100%) | 49,102 mg (100%) | 1/128 (100%) | 1497 mls (100%) |
| Cryoprecipitate Pool | 5,409 mg (4%) | 981 mg (33%) | 2,448 mg (5%) | 1/128 (6%) | 90 mls (6%) |
| Cold-Insoluble Cryoprecipitate | 1,208 mg (0.9%) | 414 mg (14%) | 132 mg (0.3%) | 1/32 (0.5%) | 27 mls (1.8%) |

The present technique could be carried out in blood bags, that is without the use of diluents. Enough heparin appears to be carried through the whole procedure so that no further additions are required. Thus the technique could be carried out readily in small collection centres.

The advantages of the present invention can be summarized by the following statements.

1. A high purity product can be obtained without the requirement for conventional protein precipitation regents or without the need for pH adjustment.

2. The procedure is simple and the technology involved is within the capabilities of a small blood bank, yet the procedure is also readily adaptable to large scale fractionation procedures.

3. The procedure can be carried out entirely in the original cryoprecipitate bag, although pooling of several bags prior to the 0° C. incubation is preferable.

4. The final product may be administered immediately, freeze dried or frozen for subsequent administration. This may be done in the bag itself or the final product may be aseptically transferred to another appropriate container as required.

5. The method is fast, requiring generally only 2 hours of incubation time at 0° C. of the resolubilized plasma cryoprecipitate, with subsequent centrifugation steps being of short duration.

6. The present method maintains Factor VIII coagulant activity and stabilizes Factor VIII during fractionation by maintaining physiological calcium level and a slightly alkaline pH.

7. The final product may be subjected to additional fractionation by conventional techniques where desired or required.

More particularly, the final product is a high yield, high purity Factor VIII concentrate at 250 units of Factor VIII per 10 ml volume, the protein content is 25 mg per ml, fibrinogen is at 8.7 mg per ml, and the heparin level is 10 units per ml. The overall recovery is 700–800 units per liter of starting plasma. The high yield and purity of the final product enable blood banks to prepare sufficient Factor VIII concentrate for hemophiliacs. Use of the present technique would provide one million Factor VIII units per 5000 to 6000 donations.

The embodiments of the invention in which an exclusive property or privilege is claimed are defined as follows:

1. In a method of obtaining Factor VIII which comprises
   (a) adding heparin to freshly obtained blood plasma collected into a calcium chelating anticoagulant or collecting blood plasma by plasma pheresis using heparin and a calcium chelating anticoagulant;
   (b) freezing the plasma;
   (c) resolubilizing the plasma;
   (d) isolating a cryoprecipitate from the plasma;
   (e) resolubilizing the cryoprecipitate;
   (f) adding a citrate saline heparin buffer to the resolubilized cryoprecipitate;
   (g) incubating the buffered, resolubilized cryoprecipitate at a temperature of from about 0° to 10° C. for a time in excess of about one hour, whereby Factor VIII present in the cryoprecipitate is insolubilized using heparin precipitable cold insoluble globulin and the resulting (Factor VIII) rich precipitate also includes cold insoluble globulin;
   (h) separating the Factor VIII rich precipitate; and
   (i) isolating Factor VIII therefrom,
   the improvement consisting of:
   (1) substituting for step (a) collecting freshly obtained blood plasma or blood plasma fractions directly into an anticoagulant consisting essentially of heparin, sodium heparin, or their mixture, in a proportion of about 6–8 units of heparin per ml of blood plasma, in the absence of a calcium chelating anticoagulant; and
   (2) substititing for step (f), adding a buffer consisting essentially of a saline heparin solution to the resolubilized cryoprecipitate, in the absence of a citrate buffer.

2. The improvement of claim 1 wherein the blood plasma is obtained from whole blood using plasma pheresis in which the anticoagulant consists essentially of heparin, sodium heparin, or their mixture, in the absence of a calcium chelating anticoagulant.

3. The improvement of claim 2 or 3 wherein about 8 units of anticoagulant are used per ml of blood plasma.

* * * * *